US006452148B1

(12) United States Patent
Bendicks et al.

(10) Patent No.: US 6,452,148 B1
(45) Date of Patent: Sep. 17, 2002

(54) OPTOELECTRONIC MONITORING DEVICE FOR A MOTOR VEHICLE

(75) Inventors: Norbert Bendicks, Hermer; Frank Blasing, Werl; Detlef Kerkmann, Nachrodt; Thomas Weber, Ludenscheid; Ralf Bobel, Dortmund; Harald Donner, Meinerzhagen, all of (DE)

(73) Assignee: Leopold Kostal GmbH & Co., Ludenscheid (DE)

( * ) Notice: Subject to any disclaimer, the term of this patent is extended or adjusted under 35 U.S.C. 154(b) by 0 days.

(21) Appl. No.: 09/508,023

(22) PCT Filed: Sep. 23, 1998

(86) PCT No.: PCT/EP98/06066

§ 371 (c)(1),
(2), (4) Date: Mar. 6, 2000

(87) PCT Pub. No.: WO99/15381

PCT Pub. Date: Apr. 1, 1999

(30) Foreign Application Priority Data

Sep. 24, 1997 (DE) .......................... 197 42 093

(51) Int. Cl.$^7$ ............................................. H01L 27/00
(52) U.S. Cl. ................................... 250/208.1; 315/77
(58) Field of Search .................. 250/208.1; 315/77, 315/82, 149–159

(56) References Cited

U.S. PATENT DOCUMENTS

| 4,288,819 A | | 9/1981 | Williams | |
|---|---|---|---|---|
| 4,867,561 A | | 9/1989 | Fujii et al. | |
| 5,172,235 A | * | 12/1992 | Wilm et al. | 358/226 |
| 5,537,003 A | * | 7/1996 | Bechtel et al. | 315/82 |
| 5,642,198 A | | 6/1997 | Long | |
| 5,796,094 A | * | 8/1998 | Schofield et al. | 250/208.1 |
| 5,837,994 A | * | 11/1998 | Stam et al. | 250/208.1 |

FOREIGN PATENT DOCUMENTS

| DE | 9104596 A | 4/1991 |
|---|---|---|
| DE | 1 15 841 A | 11/1992 |
| DE | 43 33 665 A | 4/1995 |
| DE | 195 17 194 A | 11/1996 |
| DE | 196 16 176 A | 10/1997 |
| EP | 0 566 397 A | 4/1993 |
| EP | 0546518 A1 * | 6/1993 |
| EP | 0 653 626 A | 11/1994 |
| EP | 0 770 868 A | 5/1997 |
| GB | 2 311 602 A | 3/1996 |
| JP | 9 126998 A | 5/1997 |

OTHER PUBLICATIONS

International Search Report, pp. 3–4, PCT/EP98/06066, Leopold Kostal GmbH & Co. KG, European Patent Office, Aug. 18, 1999.
Patent Abstracts of Japan, vol. 010, No. 109 (M–472), Apr. 23, 1986 & JP 60 240545 A (Nippon Denso KK), Nov. 29, 1985.

* cited by examiner

Primary Examiner—Stephone Allen
Assistant Examiner—Eric Spears
(74) Attorney, Agent, or Firm—Brooks & Kushman, P.C.

(57) ABSTRACT

An optoelectronic monitoring device for a vehicle includes a single optical sensor array having a grid of optical sensor elements. Each optical sensor element generates an electronic signal in response to optical signals imaged onto the optical sensor elements. Optical imaging systems image respective optical signals onto the optical sensor array. The optical signals of each optical imaging system is representative of a monitored condition of a vehicle. The optical imaging systems form a single physical unit which is fixed with respect to the optical sensor array. Each optical imaging system is associated with a respective optical sensor element group of the optical sensor array such that the respective optical signal of each optical imaging system is imaged onto the respective optical sensor element group. The optical sensor elements are configurable by a processor to be arranged in optical sensor element groups for being associated with respective optical imaging systems.

16 Claims, 2 Drawing Sheets

OPTOELECTRONIC MONITORING DEVICE FOR A MOTOR VEHICLE

TECHNICAL FIELD

The invention relates to an optoelectronic monitoring device for a motor vehicle.

BACKGROUND ART

For example. a monitoring device of this type is disclosed in U.S. Pat. No. 4,867,561 and is used as a rain sensor and consists of an imaging system for imaging water droplets, which are located on the windscreen, on an optoelectronic sensor array which is formed as a CCD-line. The rain sensor comprises an IR-light-emitting unit, whose light for detecting water droplets on the windscreen is directed towards said windscreen and wherein the emitted light is reflected in the event of water droplets being present on the windscreen. The reflected light is directed to an imaging convex lens, behind which is disposed the CCD-line as a photoelectric sensor array. In this case, the lens is used as an imaging system for the purpose of imaging the optical information which is to be detected by the sensor array.

In one embodiment of this previously known rain sensor, two IR-light sources can be used, wherein one is coordinated with the outer surface of the windscreen and the other is coordinated with the inner surface of the windscreen. As a consequence it is possible to differentiate between rain drops located on the outer side of the windscreen and water droplets (condensation) located on the inner side of the windscreen. For this purpose a predetermined number of adjacent transducer elements of the CCD-line is combined to form transducer element groups for evaluation purposes. In so doing, such a group can be allocated to the light source which is provided for the purpose of detecting rain drops, and a further group can be allocated to the light source which is provided for the purpose of detecting condensation.

On the whole this previously known device represents a rain or moisture sensor which can be used exclusively to ascertain whether water droplets are present on the outer side or on the inner side of a windscreen.

In the automotive industry, optical sensors are also used for the purpose of detecting further optical information. For example sensor systems of this type are used for detecting solar altitude, for controlling the headlamps or for monitoring the internal compartment of a vehicle. All of these systems have corresponding photoelectric sensor arrays and corresponding imaging systems.

SUMMARY OF THE INVENTION

On the basis of this discussed prior art, it is therefore the object of the invention to propose an optoelectronic monitoring device which renders it possible to detect different optical information of different optical sensor systems.

This object is achieved in accordance with the invention by means of an optoelectronic monitoring device for a motor vehicle having optical imaging systems which are allocated to a plurality of different monitoring objects and which on the output side influence the photosensitive surface of a photoelectric sensor array, consisting of a plurality of photoelectric transducer elements which form individual pixels, in a two-dimensional arrangement which transducer elements generate an electric signal, which corresponds to the light intensity, in dependence upon their respective exposure to light, wherein for the purpose of imaging the optical information which is provided by the imaging system, the output of each imaging system is disposed above a transducer element group which is allocated to this imaging system and consists of one or several transducer elements, and having an evaluation unit which is influenced by virtue of the electric output signals of the sensor array for the purpose of controlling actuators in dependence upon the result of an evaluation of the information relating to the object, which imaging systems are combined in the region of their outputs to form a physical unit and are fixed on a circuit carrier which is allocated to the sensor array.

By virtue of the monitoring device in accordance with the invention, which is allocated a plurality of imaging systems supported expediently by a common holding device which combines the imaging systems, this monitoring device can be used for the most varied optical sensor systems by using a single sensor array. Imaging systems include both image-forming systems, i.e. lenses, or optic fiber systems. Since the output of each imaging system is allocated a predetermined transducer element group of the sensor array, it is possible to allocate in a defined manner predetermined group signals to predetermined imaging systems and thus to predetermined optical information which is to be detected. It is possible that between the individual transducer element groups there are provided transducer element gaps or lines which are not allocated to an imaging system. These transducer elements would render it possible to control the exposure corresponding to the ambient light or to determine the continuous ambient light.

The individual imaging systems are combined in the region of the photoelectric sensor array to form a physical unit and are fixed on the circuit carrier of the sensor array. Therefore, the sensor array is held in a fixed position with respect to the outputs of the imaging systems, so that always the same transducer elements are influenced by the imaging systems even in the event of vehicle vibrations.

When a photoelectric sensor array which is used in a motor vehicle is provided with a lens as one of the imaging systems, the said sensor array is suitable for detecting image-forming information. This type of system can therefore be used, for example, as an internal vehicle compartment monitoring system or also for monitoring the area surrounding the vehicle, i.e. for the purpose of receiving signals in a distance sensing system. When using this sensor array for monitoring the internal compartment of a vehicle, it is expedient to dispose such a sensor array in the region of the internal rearview mirror or in the region of a roof console as a roof module, so that it operates in a rearward direction. The remaining optical information is supplied to the sensor array by means of optic fibers as further imaging systems wherein individual fibers can be used for the purpose of transmitting light intensities or fiber bundles can be used for the purpose of transmitting image-forming information.

This type of photoelectric sensor array having a multi-functional lens system formed by the combination of different imaging systems can also be disposed in a different position in a motor vehicle. The optical information supplied to the sensor array can be filtered with regard to the information which is to be actually detected. Since the sensor array can be formed for the purpose of receiving a large frequency bandwidth, this type of sensor array is suitable at the same time for a wide range of optical sensing systems which can use both IR-light, visible light or UV-light.

In one advantageous embodiment a type of sensor array is provided, whose individual transducer elements can be addressed and selected in a free manner. This type of embodiment produces advantages particularly with respect to an alignment of the sensor array-side outputs of the imaging systems with respect to the photosensitive surface of the sensor array when the two elements are assembled and in the interests of guaranteeing consistent quality. Owing to the similar formation of all of the transducer elements of the sensor array, this design allows the spatial position of a transducer element group to be defined using software. It is then possible to use the software to adjust the transducer element groups in relation to the respective imaging systems. Consequently, it is possible to compensate for any assembly inaccuracies in the arrangement of the imaging systems with respect to the sensor array; the individual transducer element groups can also be adapted using software to suit any changes as a result of operation over a period of many years or as a result of other causes which lead to a deviation in the transducer element group which is defined for an imaging system.

Further advantages of the invention and embodiments are included in the remaining subordinate claims and in the description herein under of one exemplified embodiment.

BEST MODES FOR CARRYING OUT THE INVENTION

Figure 1:
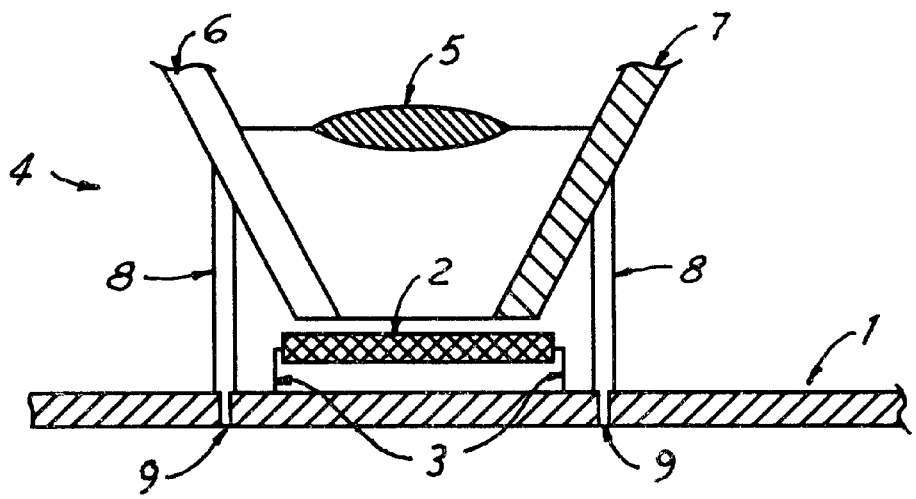
FIG. 1 shows a schematic sectional view of a photoelectric sensor array having a plurality of imaging systems of an optoelectronic monitoring device for a motor vehicle.

A photoelectric sensor array 2 is attached to a printed circuit board 1 in an electrically contacting manner by means of conductor tracks which correspond to its contact feet 3. The photoelectric sensor array 2 is a square camera sensor chip, whose photosensitive surface is formed by a plurality of individual transducer elements (pixels). In the case of the illustrated photoelectric sensor array, square pixels are provided, so that the sensor array 2 comprises a line pixel number which corresponds to the gap pixel number. The individual pixels of the camera sensor chip 2 can be addressed and selected in a free manner.

Above the sensor array 2 is disposed a multi-functional lens system 4 which is held in a holding device [not illustrated in detail]. The multi-functional lens system 4 represents an lens system group, in which a plurality of imaging systems 5, 6, 7 are combined. The imaging systems 5, 6, 7 supply the photosensitive surface of the sensor array 2 with the optical information required for the purpose of detecting predetermined systems. The imaging system 5 is an imaging lens system, namely a convex lens; the imaging systems 6, 7 are in each case optic fibers which supply the required optical information from the actual detection site to the sensor array 2. The imaging system 5 in the exemplified embodiment illustrated in FIG. 1 serves to monitor the internal compartment of a motor vehicle. The imaging systems 6, 7 serve to illustrate a rain sensing system or a solar altitude sensing system.

The multi-functional lens system 4 or the holding device for the lens system group is supported by way of feet 8 and is held and attached on the printed circuit board 1 in collecting bores 9.

It is evident in the illustration in FIG. 1 that when assembling both the camera sensor chip 2 and the multi-functional lens system 4 tolerance inaccuracies can occur with respect to the allocation of the output of an imaging system 5, 6 or 7 to a predetermined pixel cluster which is allocated to these outputs. Software-controlled pixel clustering can be used to adjust in an exact manner the units 2, 4 with respect to each other, said adjustment process being adapted to suit the actual outputs of the imaging systems 5, 6, 7 after the units 2, 4 have been assembled on a printed circuit board 1, so that precisely those pixels of the sensor array 2 which are also actually influenced by light by the output of this type of imaging system 5, 6, 7 are allocated to the respective output of an imaging system 5, 6, 7. For this purpose, the individual pixels can be addressed in a free manner. Accordingly, slower changes as a result of the operation of this system can be compensated for.

Figure 2:
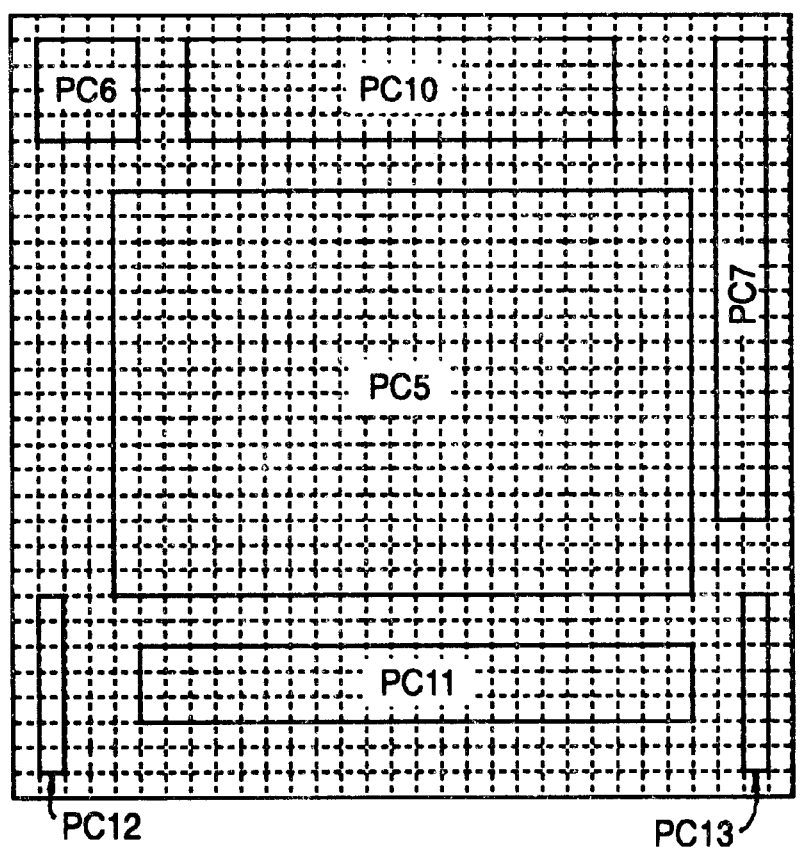
FIG. 2 shows an enlarged plan view of the sensor array shown in FIG. 1.

The plan view shown in FIG. 2 of the photosensitive side of the camera sensor chip 2 illustrates the clustering of the pixels. The imaging system 5 is allocated the pixel cluster PC 5, the imaging system 6 is allocated the pixel cluster PC 6 and the imaging cluster 7 is allocated the pixel cluster PC 7. In addition to the imaging systems 5, 6, 7 the multi-functional lens system 4 contains further imaging systems which for the sake of clarity are not illustrated in FIG. 1 and whose pixel clusters are designated in FIG. 2 by PC 10, PC 11, PC 12 and PC 13. The individual pixel clusters PC 5, PC 6, PC 7, PC 10, PC 11, PC 12, PC 13 are not immediately adjacent to each other, but are separated from each other by virtue of individual pixel rows or gaps. These pixels which are not directly allocated to the output of an imaging system can either be unused and thus not controlled by software, or else they can be used for the purpose of controlling the exposure or for determining the continuous ambient light.

In a further exemplified embodiment [not illustrated], the outputs of the imaging systems used are disposed in such a manner that they are quasi immediately adjacent to each other but do not influence each other.

By virtue of the ability to select the individual pixel clusters PC 5, PC 6, PC 7, PC 10, PC 11, PC 12, PC 13 in a free manner the signals can be directed to separate evaluation processes. Accordingly, it is possible to allocate a different level of significance or different priorities to the individual pixel clusters PC 5 to PC 13 which serve to establish the order of priority in which the said pixel clusters are selected. The camera sensor chip 2 is connected to a processor unit [not illustrated in the Figures], which serves to select the individual pixel clusters PC 5 to PC 13 of the camera sensor chip 2 according to a predetermined algorithm.

Figure 3:
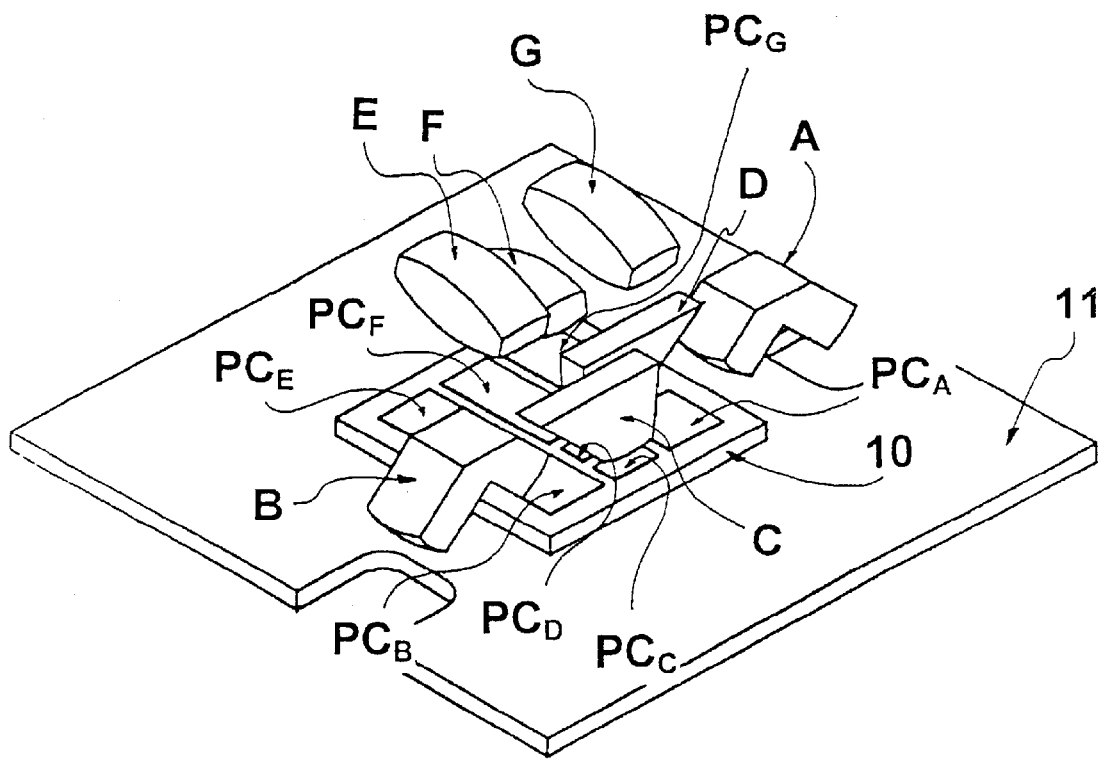
FIG. 3 shows a schematic view of a further photoelectric sensor array having a plurality of imaging systems of an optoelectronic monitoring device for a motor vehicle.

FIG. 3 schematically illustrates in a type of perspective view the receiving unit of a further optoelectronic monitoring device for a motor vehicle. The receiving unit comprises in turn a surface camera chip 10 which is mounted on a carrier plate 11. A plurality of imaging systems A–G are combined in a holding device [not illustrated in detail] and these imaging systems are held by said holding device in their position, shown in FIG. 3, with respect to the photosensitive surface of the surface camera chip 10. The imaging systems A–G supply optical information from different monitoring objects to the surface camera chip 10. Each imaging system A–G is allocated a discrete pixel cluster $PC_A$–$PC_G$. The imaging systems E–G are image-forming imaging systems, wherein the lens systems illustrated in FIG. 3 are formed as convex lenses. The remaining imaging systems A–D serve to transmit light-imaging information, such as e.g. differences in brightness.

It is particularly advantageous to produce the imaging systems A–G from a synthetic material wherein the illustrated lens system groups are mutually connected by virtue of cross-pieces. The cross-pieces then represent the common holding device of the imaging systems A–G and they are supported by way of feet on the carrier plate 11. It can be provided that these imaging systems which are held together can be connected to the carrier plate 11 by virtue of a locking plug-in procedure.

In one embodiment it is provided that individual pixel clusters are not selected in a uniform manner but are selected blockwise segmented into blocks, as disclosed in U.S. Pat. No. 4,867,561.

It is evident in the illustration of the invention, that the described photoelectric sensor array having its multi-functional lens system is suitable for numerous applications and the application in the automotive industry is taken as the example in this case. The ability to arrange this type of system in a central manner also has a favorable effect upon the variability of this type of system, for example if a multi-functional lens system comprises free receiving arrangements for the subsequent installation of additional imaging systems. By simply reprogramming the pixel clusters or by additionally activating predetermined pixel clusters, the camera sensor chip 2 can be adjusted accordingly.

What is claimed is:

1. An optoelectronic monitoring device for a motor vehicle comprising:

a single optical sensor array having a two dimensional grid of optical sensor elements, each of the optical sensor elements generating an electronic signal in response to optical signals imaged onto the optical sensor elements; and a plurality of optical imaging systems for imaging optical signals onto the optical sensor array, the optical signals of each optical imaging system respectively representative of a different monitored condition associated with a motor vehicle, wherein the optical imaging systems are combined to form a single physical unit which is fixed with respect to the optical sensor array, wherein each optical imaging system is associated with a respective optical sensor element group of the optical sensor array such that the respective optical signal of each optical imaging system is imaged onto the respective optical sensor element group of the optical sensor array.

2. The device of claim 1 wherein:

each optical sensor element group has at least one optical sensor element.

3. The device of claim 1 wherein:

each of the optical sensor element groups has optical sensor elements different from the optical sensor elements of the other optical sensor element groups.

4. The device of claim 1 wherein:

an optical sensor element group generates an electronic signal in response to an optical signal of a respective optical imaging system imaged onto the optical sensor element group for controlling the motor vehicle as a function of the monitored motor vehicle condition associated with the imaged optical signal.

5. The device of claim 1 wherein:

the optical imaging systems are fixed in position with respect to the optical sensor array.

6. The device of claim 1 wherein:

each optical imagine system is disposed adjacent to its respective optical sensor element group of the optical sensor array.

7. The device of claim 1 wherein:

the optical imaging systems are disposed over the optical sensor array.

8. The device of claim 1 wherein:

the optical sensor elements of the optical sensor array are configurable by a processor to be arranged in optical sensor element groups for being associated with respective optical imaging systems.

9. The device of claim 1 wherein:

at least one of the optical imaging systems includes an image forming lens for imaging optical signals.

10. The device of claim 1 wherein:

at least one of the optical imaging systems includes an optic fiber for imaging optical signals.

11. The device of claim 1 wherein:

an optical sensor element group generates an electronic signal in response to an optical signal of a respective optical imaging system imaged onto the optical sensor element group for controlling a motor vehicle function as a function of a monitored motor vehicle condition associated with the imaged optical signal.

12. The device of claim 1 wherein:

an optical sensor element group generates an electronic signal in response to an optical signal of a respective optical imaging system imaged onto the optical sensor element group for controlling the motor vehicle as a function of rain monitored by the respective optical imaging system.

13. The device of claim 1 wherein:

an optical sensor element group generates an electronic signal in response to an optical signal of a respective optical imaging system imaged onto the optical sensor element group for controlling the motor vehicle as a function of solar attitude monitored by the respective optical imaging system.

14. The device of claim 1 wherein:

an optical sensor element group generates an electronic signal in response to an optical signal of a respective optical imaging system imaged onto the optical sensor element group for controlling motor vehicle headlamps as a function of light monitored by the respective optical imaging system.

15. The device of claim 1 wherein:

each of the optical sensor elements generate an electronic signal in response to optical signals imaged onto the optical sensor elements as a function of the intensity of the optical signals.

16. An optoelectronic monitoring device for a motor vehicle comprising:

a single optical sensor array having a two dimensional grid of optical sensor elements, each of the optical sensor elements generating an electronic signal in response to optical signals imaged onto the optical sensor elements; and a plurality of optical imaging systems for imaging optical signals onto the optical sensor array, the optical signals of each optical imaging system respectively representative of a different monitored condition associated with a motor vehicle, wherein the optical imaging systems are combined to form a single physical unit which is fixed with respect to the optical sensor array, wherein each optical imaging system is associated with a respective optical sensor element group of the optical sensor array such that the respective optical signal of each optical imaging system is imaged onto the respective optical sensor element group of the optical sensor array, wherein the optical sensor elements of the optical sensor array are configurable by a processor to be arranged in optical sensor element groups for being associated with respective optical imaging systems.

* * * * *